United States Patent [19]

Csányi et al.

[11] Patent Number: 5,110,720
[45] Date of Patent: May 5, 1992

[54] DENTAL COMPOSITION AND A PROCESS FOR THE PREPARATION THEREOF

[75] Inventors: Endre Csányi; Gábor Csányi; Tibor Balogh; László Nagy, all of Budapest, Hungary

[73] Assignee: Reanal Einomvegyszergyar, Budapest, Hungary

[21] Appl. No.: 381,722

[22] PCT Filed: Jan. 29, 1988

[86] PCT No.: PCT/HU88/00003
§ 371 Date: Jun. 28, 1989
§ 102(e) Date: Jun. 28, 1989

[87] PCT Pub. No.: WO88/05650
PCT Pub. Date: Aug. 11, 1988

[51] Int. Cl.$^5$ ............................................. A61C 5/00
[52] U.S. Cl. .................................. 433/215; 433/217.1
[58] Field of Search .............................. 433/215, 217.1

[56] References Cited

U.S. PATENT DOCUMENTS 3,913,229 10/1975 Driskell et al. .
4,121,940 10/1978 Michel et al. .

FOREIGN PATENT DOCUMENTS

| 0667808 | 11/1938 | Fed. Rep. of Germany . |
| 1195436 | 6/1965 | Fed. Rep. of Germany . |
| 1202937 | 10/1965 | Fed. Rep. of Germany . |
| 2321215 | 11/1973 | Fed. Rep. of Germany . |
| 2629694 | 1/1977 | Fed. Rep. of Germany . |
| 3539202 | 5/1986 | Fed. Rep. of Germany . |
| 1465406 | 2/1977 | United Kingdom . |

Primary Examiner—V. Millin
Attorney, Agent, or Firm—Keil & Weinkauf

[57] ABSTRACT

The invention is directed to compositions for use in dental preparations which comprise an anti-osteoporotic agent, particularly ipriflavone, an anti-phlogistic agent, particularly triamcinolone, and, optionally, a natural or synthetic chemotherapeutic agent or local anaesthetic. The invention is also directed to methods for preparation of the compositions and methods of their use for treating caries and for the healing of acute, subacute or chronic inflammatory lesion of pulp, dental radix or the bony substance surrounding them.

8 Claims, No Drawings

DENTAL COMPOSITION AND A PROCESS FOR THE PREPARATION THEREOF

The invention relates to a new dental composition and to a process for the preparation thereof.

As known, caries is the most widespread endemic disease. It is quite obvious to one skilled in the art that a great deal of teeth could be saved by a preservative treatment performed in due time. In practice, however, patients turn to the dentist only when they suffer from an untolerable pain, i.e. when at least one complication exists, too.

Pain is caused first by pulp hyperaemia, i.e. by the reversible inflammation of the vessels and intravascular nerves of the dental radix. The volume of the narrow pulp canal, closed between hard walls, cannot increase, thus the arteries exert a hard pressure on the veins, which results in an early appearance of venal hyperaemia. At the stage of pulp hyperaemia, however, caries does not reach the pulp, since it is separated from it by a thin healthy layer of dentin.

When caries proceeds, an infectious inflammation appears in the pulp (pulpitis). Of the various forms of pulpitis only the main types are mentioned now. When an acute inflammation exists and the pulp is only partially damaged, dentists endeavour to save the living tooth. When inflammation gets, however, cronic and the pulp is completely damaged, the goal of dental treatment is to render the further treatment painless, to exclude additional complications and to ensure a symptom-free recovery.

In its final stage, pulpitis leads to gangrene. Tooth necrosis does not terminate, however, in the pulp. The defensive mechanism of the organism can act against infections only at territories with good blood supply. Periodontium, which surrounds the tooth, suits this requirement, consequently the next stage is the appearance of periodontitis. At the appearance of this disorder, causing pains even upon touch, pulp itself is no longer sensitive, the subjective symptoms are, however, very painful. The task of dentists is to ensure the quick alleviation of this complaint in the acute stage of inflammation. In chronic stages, however, additional complications must be taken into account. Inflammation may spread over the periodontal bony substance where it may lead to pathologic osteoporoses (granuloma, cysts).

Several attempts have been made to defend the exacerbation of the above diseases. According to Adler and Zaray [Konzerváló fogászat (Preservative Dentistry) p. 172 (Medicina, Budapest, 1972) (in Hungarian)] pulp canal must be sterilized completely. It is very important that the surrounding tissues be free of inflammation. Therefore pulp canal has been treated with various sterilizing agents, antibiotics and antiphlogistics, utilized most frequently as a liquid composition. A disadvantage of this method is that prolonged activity cannot be ensured.

Utilization of powders or removable pastes in such treatments has also been attemped [Fogorvosi Szemle (Dentists' Review) 64, 404 (1971) (in Hungarian)], but prolonged effect could not be achieved.

Hungarian patent No. 167,308 suggests the use of pointers comprising a sterilizing (i.e. oxidizing) or antiphlogistic agent and/or an antibiotic in admixture with an inert plastic carrier. Penicillin, chloramphenicol and oxytetracyclin are mentioned as antibiotics, whereas hydrocortisone is mentioned as antiphlogistic agent.

The major disadvantage of this method is that it can be applied only for the treatment of excavated pulp canal, furthermore it cannot act against osteoporosis coupled with other complications.

The invention aims at providing a new composition applicable for the treatment of caries and for the healing of acute, subacute or chronic inflammatory lesions of pulp, dental radix or the bony substance surrounding them.

Our extensive experimental work has led to the unexpected recognition that a particular combination, i.e. a combination of ipriflavone (7-isopropoxy-isoflavone) and an antiphlogistic agent can be utilized with good results for the complex treatment of teeth. Depending on the conditions of use, this combination can be supplemented with chemotherapeutic agents, local anaesthetics and known auxiliary agents.

The above combination can be applied successfully in all stages of pulpitis and periodontitis.

Based on the above, the invention relates to a new dental composition comprising an anti-osteoporotic agent, preferably ipriflavone, an antiphlogistic agent, optionally a natural or synthetic chemotherapeutic agent or a local anaesthetic, furthermore one or more known auxiliary agent(s).

The invention also relates to a process for the preparation of the above dental composition. According to the invention 0.1 to 30% by weight of ipriflavone, 0.5 to 15% by weight of an antiphlogistic agent, preferably triamcinolone, and optionally one or more natural or synthetic chemotherapeutic agent(s) or local anaesthetic(s) are admixed with auxiliary agents commonly applied in dentistry. As synthetic chemotherapeutic agents e.g. sulphonamides or trimethoprim [2,4-diamino-5-(3',4',5'-trimethoxybenzyl)pyrimidine], whereas as natural chemotherapeutic agent e.g. doxycyclin base (an antibiotic) or a salt thereof can be applied. As local anaesthetic [required e.g. to prepare a coating for protecting dental stump] lidocaine can be used. Of the sulphonamides sulphamethoxazole is particularly preferred. The known auxiliary agents for dental purposes are e.g. zinc oxide, calcium oxide, bismuth oxide, titanium dioxide, eugenol, epoxy resin and dental lacquers.

The utilization of more than one active agent in a dental filler has led to particularly advantageous and unexpected results.

The antimicrobial agent with a broad spectrum of activity is utilized to exterminate the pathogens which cause inflammation. The antimicrobial agent alone does not act on the other components of the inflammatory process.

Triamcinolone, utilized as antiphlogistic agent, exerts a very strong effect on the inflammatory process: it suppresses the oedema and stops the other inflammatory components, resulting in a quick alleviation of pain and in the cessation of inflammation. It is known, however, that this substance may also enhance the activity of osteoklasts causing osteoporosis in the bony substance e.g. when a triamcinolone-containing filling agent is introduced into the pulp canal after the removal of pulp.

Ipriflavone, one of the members of the combination according to the invention, supplements the effects of the two former components in a particularly advantageous manner: it is able to suppress osteoporosis even alone, furthermore it antagonizes the osteoklast activity-increasing effects of steroidal antiphlogistics.

By combining these three types of active agents a series of therapeutic dental fillers, suitable for preserving the teeth in any stage of pulpitis and periodontitis, can be obtained.

The most important advantage provided for by the invention is that the combination can be utilized in several types of dental diseases. The new combinations can be utilized for the following purposes:

1. In the treatment of pulp hyperaemia and acute partial pulpitis a dental cement comprising 0.1 to 10%, preferably 0.7 to 2% of the combination according to the invention should be placed onto the pulp-side wall of the cavity formed by the dentist, wherefrom the active agents enter the pulp and result in a very quick relief of pain and in the suppression of inflammation. Doxycyclin, mentioned as an example of the chemotherapeutic agents, accumulates in the tooth, resulting in a prolonged effect. Upon the effect of ipriflavone the formation of secondary dentin is also to be expected.

2. In chronic total pulpitis the treatment is performed in two steps. First the treatment described in point 1 above is performed in order to attain a painless stage, thereafter the pulp canal is excavated to prevent the spreading of inflammation, and in the second treatment step the method described in point 3 below is performed.

3. In the treatment of periodontitis the therapeutic paste (admixed with appropriate auxiliary agents) is applied into the previously cleaned and dried pulp canal. The antiphlogistic and antimicrobial effects appear quickly, and a very quick relief of pain is to be expected.

4. When the complications of periodontitis are to be avoided or the already existing complications should be suppressed, the reversal of osteoporoses already formed (ostitis diffusa, granuloma, cysts) is to be expected upon a prolonged application of the anti-osteoporotic therapeutic paste. The final root filling is prepared after the termination of the complete bony defects, utilizing an antibiotic-free composition comprising anti-osteoporotic agents, X-ray contrast materials and carriers.

The invention is elucidated in detail by the aid of the following non-limiting Examples.

EXAMPLE 1

Preparation of a therapeutic cement

A mixture of 2 g of doxycyclin hyclate, 0.8 g of triamcinolone, 2.0 g of ipriflavone, 80 g of zinc oxide and 15.2 g of calcium oxide (Component "A") is admixed with eugenol (Component "B") in a ratio to obtain a composition with a consistency required in dentistry.

EXAMPLE 2

Preparation of a therapeutic cement

One proceeds as described in Example 1 with the difference that doxycyclin hyclate is replaced by 2.2 g of trimethoprim.

EXAMPLE 3

Preparation of a therapeutic paste for sterilizing pulp canal 0.2 g of ipriflavone is admixed with 0.2 g of doxycyclin base, 0.08 g of triamcinolone and 10 g of zinc oxide, and the mixture is completed with eugenol in an amount required to obtain a paste.

EXAMPLE 4

Preparation of a therapeutic paste for sterilizing pulp canal

One proceeds as described in Example 3 with the difference that sulphamethoxazole is substituted for doxycyclin base.

EXAMPLE 5

Preparation of a root filler 0.5 g of ipriflavone are admixed with 0.1 g of triamcinolone, 4.0 g of bismuth oxide, 2.0 g of titanium dioxide and 3.4 g of zinc oxide, and epoxy resin is added to the mixture in an amount to obtain a paste.

EXAMPLE 6

Preparation of a coating composition for protecting dental stump

A mixture of 0.3 g of ipriflavone, 0.1 g of triamcinolone and 0.2 g of lidocaine base is dissolved in 5 ml of acetone. This solution can be utilized for the preparation of a single coating or multiple coatings.

What we claim is:

1. A dental composition which comprises an anti-osteoporotic agent, an antiphlogistic agent, one or more known auxiliary agent(s), optionally, a natural or synthetic chemotherapeutic agent and, optionally, a local anaesthetic.

2. The composition of claim 1, which comprises ipriflavone (7-isopropoxyisoflavone) as the anti-osteoporotic agent, triamcinolone as the antiphlogistic agent, an antibiotic, a sulphonamide or trimethoprim as a chemotherapeutic agent and lidocaine as the local anaesthetic.

3. The composition of claim 2, which comprises 0.1 to 30% by weight of ipriflavone, 0.5 to 15% by weight of triamcinolone, 0 to 10% by weight of doxycyclin or a salt thereof, 0 to 20% by weight of lidocaine, and 35 to 99.4% by weight of one or more known auxiliary agent(s).

4. A process for the preparation of a dental composition, characterized in that 0.1 to 30% by weight of ipriflavone, 0.5 to 15% by weight of triamcinolone, 0 to 10% by weight of doxycyclin or a salt thereof and 0 to 20% by weight of lidocaine are admixed with 35 to 99.4% by weight of one or more known auxiliary agent(s).

5. A method for protecting pulp of carious teeth, which comprises applying an effective amount of the composition of claim 1 to the infected area.

6. A method for preserving the vitality of pulp in the early stages of pulpitis, which comprises applying an effective amount of the composition of claim 1 to the infected area.

7. A method for sterilizing a pulp canal, which comprises applying an effective amount of the composition of claim 1 to the pulp canal.

8. A method for preparing a final root filling, which comprises utilizing the composition of claim 1 and an X-ray contrast agent as the filling material.

* * * * *

UNITED STATES PATENT AND TRADEMARK OFFICE
CERTIFICATE OF CORRECTION

PATENT NO. : 5,110,720

DATED : May 5, 1992

INVENTOR(S) : Endre CSANYI, Gabor CSANYI, Tibor BALOGH, Laszlo NAGY

It is certified that error appears in the above-identified patent and that said Letters Patent is hereby corrected as shown below:

On title page, item [73], delete "Einomvegyszergyar" and insert therefor ---Finomvegyszergyar--.

Signed and Sealed this

Thirteenth Day of July, 1993

Attest:

MICHAEL K. KIRK

Attesting Officer     Acting Commissioner of Patents and Trademarks